United States Patent [19]
Baker

[11] Patent Number: 5,135,532
[45] Date of Patent: Aug. 4, 1992

[54] DRILL HEAD ASSEMBLY FOR CRANIAL PERFORATORS

[76] Inventor: John W. Baker, 4 Wachusett Dr., Acton, Mass. 01720

[21] Appl. No.: 494,765

[22] Filed: Mar. 16, 1990

Related U.S. Application Data

[60] Continuation-in-part of Ser. No. 299,084, Jan. 23, 1989, Pat. No. 4,951,690, which is a division of Ser. No. 781,933, Sep. 30, 1985, Pat. No. 4,884,571, which is a continuation-in-part of Ser. No. 575,571, Jan. 31, 1984, Pat. No. 4,600,006.

[51] Int. Cl.[5] .............................................. A61B 17/16
[52] U.S. Cl. ..................... 606/173; 408/206; 408/225
[58] Field of Search ................... 408/14, 15, 139, 703, 408/206, 225; 606/80, 81, 172, 173, 179, 180

[56] References Cited

U.S. PATENT DOCUMENTS

| | | | |
|---|---|---|---|
| 1,910,143 | 5/1933 | Arenz | 408/213 |
| 2,358,077 | 9/1944 | Koett | 408/213 |
| 2,525,669 | 10/1950 | Hainault | 606/173 |
| 2,842,131 | 7/1958 | Smith | 606/173 |
| 2,883,888 | 4/1959 | Stewart | 408/214 |
| 3,543,820 | 12/1970 | Tulumello | 408/199 |
| 4,319,577 | 3/1982 | Bofinger et al. | 408/224 |
| 4,362,161 | 12/1982 | Reimels et al. | 606/173 |
| 4,600,006 | 7/1986 | Baker | 606/173 |
| 4,803,982 | 2/1989 | Baker | 606/173 |
| 4,884,571 | 12/1989 | Baker | 408/206 |
| 4,951,690 | 8/1990 | Baker | 606/173 |

Primary Examiner—C. Fred Rosenbaum
Assistant Examiner—William W. Lewis
Attorney, Agent, or Firm—Pandiscio & Pandiscio

[57] ABSTRACT

A drill head assembly for a cranial perforator, which assembly is similar to the drill head assembly disclosed in U.S. Pat. No. 4,884,571, except that the configuration of the axially-projecting sections of the front end surfaces of the inner drill are modified to cause the inner drill to stop rotating more quickly upon penetration of the inner drill through a skull.

20 Claims, 2 Drawing Sheets

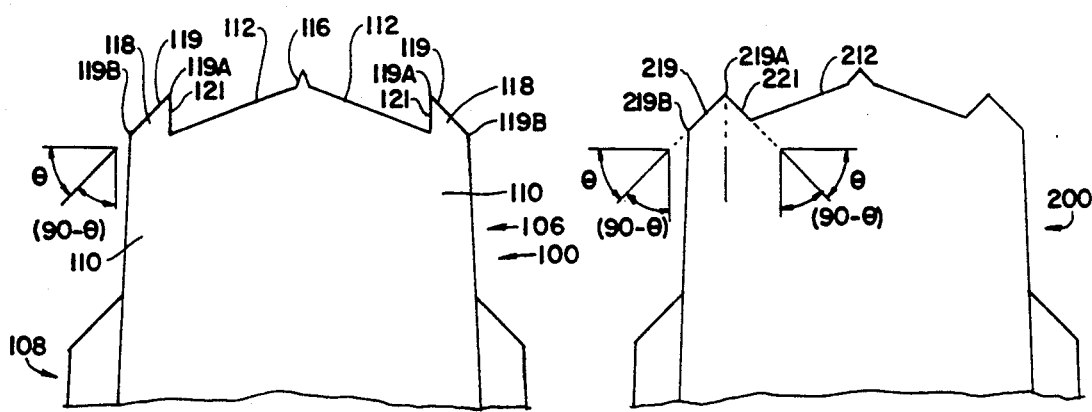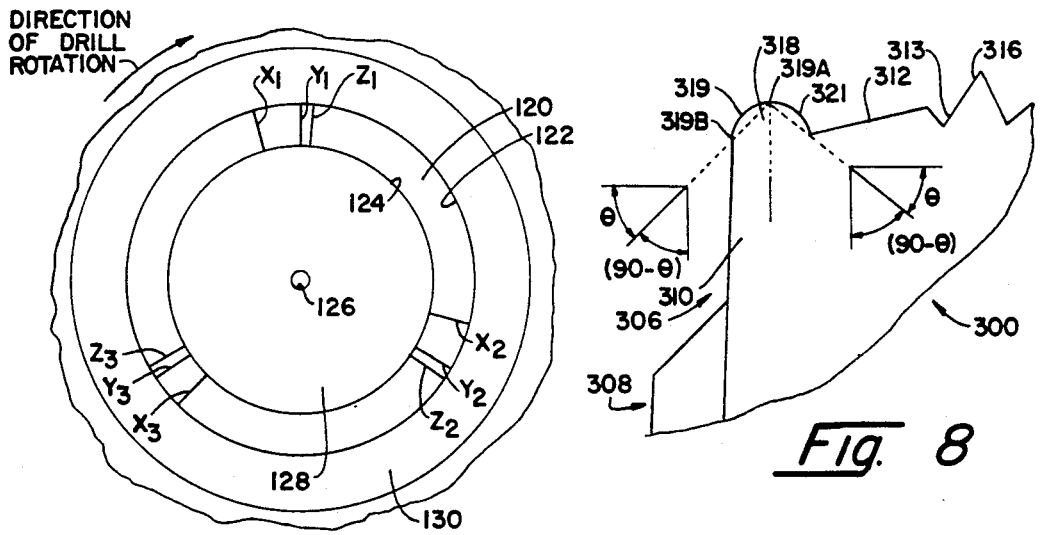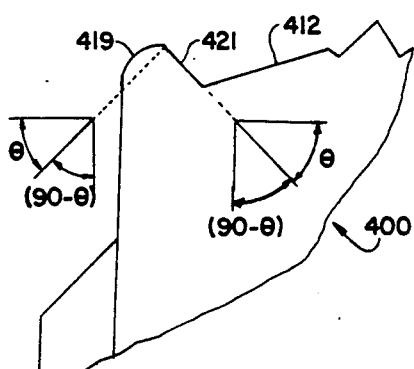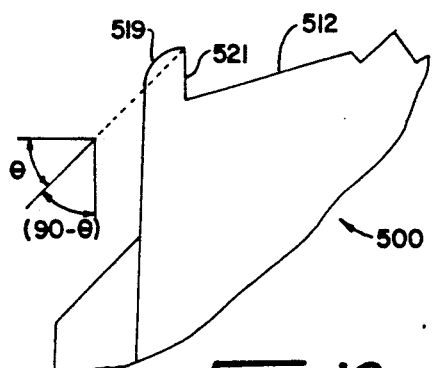

DRILL HEAD ASSEMBLY FOR CRANIAL PERFORATORS

REFERENCE TO RELATED APPLICATIONS

This is a continuation-in-part of U.S. patent, application Ser. No. 07/299,084, filed Jan. 23, 1989, (now U.S. Pat. No. 4,951,690) which is a divisional of U.S. patent application Ser. No. 781,933, filed Sep. 30, 1985 (now U.S. Pat. No. 4,884,571, issued Dec. 5, 1989), which is itself a continuation-in-part of U.S. patent application Ser. No. 575,571, filed Jan. 31, 1984 (now U.S. Pat. No. 4,600,006, issued Jul. 15, 1986).

FIELD OF THE INVENTION

This invention relates to cranial perforators of the sort used to bore holes through the skull, and more particularly to the cutting surface configurations of such cranial perforators.

BACKGROUND OF THE INVENTION

Cranial perforators are special purpose drills which are used to bore holes through the skull during cranial surgery. Such holes may be needed to vent fluids from the region surrounding the brain, to provide small passageways to the brain for the insertion and removal of instruments, or to position a cranial saw for subsequent use in removing a larger piece of the skull.

Regardless of the end use of the hole being made, it is critical that the cranial perforator cease its boring action as quickly as possible after it passes through the skull and, if possible, before it encounters, and thereby damages, the delicate dura tissue surrounding the brain, or the brain itself. To this end, cranial perforators have traditionally utilized a special "safety construction" designed to permit forward penetration by the perforator only so long as the perforator's leading tip is encountering bone, and to halt forward penetration by the perforator as quickly as possible after the perforator's leading tip passes through the bone and, hopefully, before it encounters the soft tissue beneath the bone. More particularly, cranial perforators have traditionally comprised a drill head assembly having a pair of drills disposed in concentric relation to one another, with the inner drill leading the outer drill so that a bore-counterbore opening is formed as the perforator penetrates into the skull. The two drills are coupled to a rear support and drive assembly via a special drive mechanism such that (1) both drills are rotatably driven so long as the leading inner drill is encountering a resistive surface (i.e., bone) and (2) both drills are no longer rotatably driven when the inner drill stops encountering the resistive surface (i.e., when the inner drill passes through the bone) while the outer drill is still encountering the resistive surface (i.e., while it is still cutting through the bone). Inasmuch as the leading inner drill and the trailing outer drill are adapted to cut in a bore-counterbore arrangement, the shoulder of bone formed at the intersection of the bore-counterbore opening automatically impedes further progress of the perforator toward the brain once the inner and outer drills are no longer rotating. As a result, the surgeon using the cranial perforator does not have to concentrate on the amount of pressure to be applied to the cranial perforator as the remaining bone becomes thinner and thinner, and generally need not fear that the perforator will plunge through the bone into the head so as to severely damage the delicate dura tissue or the brain itself. Such cranial perforators have included both reusable, disposable and disposable tip models.

U.S. Pat. No. 4,600,006, issued Jul. 15, 1986 to John W. Baker for "Cranial Perforator", discloses an improved form of cranial perforator incorporating the foregoing "safety construction". Still other cranial perforators incorporating the foregoing "safety construction" are disclosed in U.S. Pat. No. 4,803,982, issued Feb. 14, 1989 to John W. Baker for "Cranial Perforator", pending U.S. patent application Ser. No. 07/423,660, filed Oct. 18, 1989, U.S. Pat. No. 4,884,571, issued Dec. 5, 1989 to John W. Baker for "Cranial Perforator With Reentrant Cutting Segment", and pending U.S. patent application Ser. No. 07/299,084, filed Jan. 23, 1989.

As noted above, the "safety construction" of the foregoing perforators is characterized by inner and outer drills which are coupled to a rear support and drive assembly via a special drive mechanism such that both drills are rotatably driven so long as the leading inner drill is encountering a resistive surface (i.e., bone) and both drills are no longer rotatably driven when the inner drill stops encountering the resistive surface (i.e., when the inner drill passes through the bone) while the outer drill is still encountering the resistive surface (i.e., while it is still cutting through the bone). However, it has been observed that even with these cranial perforators, the inner drill continues to rotate some angular amount after the inner drill has penetrated the skull.

A portion of the aforementioned post-penetration angular rotation of the inner drill is associated with the design of the special drive mechanism employed in the perforators, which consists of cams and cam followers which withdraw engaging portions of the inner drill forward out of driving engagement with the rear support and drive assembly. Details on the design and function of this special drive mechanism are provided in U.S. Pat. No. 4,600,006, which is incorporated herein by reference. For convenience, the portion of the aforementioned post-penetration angular rotation of the inner drill associated with the disengagement of the inner drill from the rear support and drive assembly will be referred to as "disengagement rotation".

Another portion of the aforementioned post-penetration angular rotation of the inner drill is associated with the angular momentum resident in the quickly rotating inner drill at the moment the inner drill disengages from the rear support and drive assembly. In effect, the angular momentum stored in the quickly rotating inner drill at the moment of full disengagement causes the inner drill to continue rotating until this angular momentum is dissipated through friction. For convenience, this portion of the aforementioned post-penetration angular rotation of the inner drill will be referred to as "momentum rotation".

The aforementioned post-penetration "disengagement rotation" is believed to be an unavoidable consequence of the special drive mechanism associated with the aforementioned cranial perforators, whereas the aforementioned post-penetration "momentum rotation" is not. Since any rotation of the inner drill after it passes through the bone increases the possibility of damaging the dura or the brain, it is desirable to stop the rotation of the inner drill as quickly as possible after the inner drill penetrates the skull.

OBJECTS AND SUMMARY OF THE INVENTION

Accordingly, the principal object of the present invention is to provide an improved drill head assembly for "safety construction" cranial perforators which will minimize any continued angular rotation of the inner drill after it passes through the skull.

Another object of the present invention is to provide an improved drill head assembly for "safety construction" cranial perforators which will substantially eliminate the aforementioned post-penetration "momentum rotation" of the inner drill.

Another object of the present invention is to provide an improved drill head for "safety construction" cranial perforators which will yield a thicker and stronger shoulder of bone adjacent the peripheral portion of the front cutting edge of the inner drill to impede further progress of the inner drill toward the brain once the drill members are disengaged from the drive assembly.

Yet another object of the present invention is to provide an improved drill head assembly which may be used with cranial perforators of the type disclosed in U.S. Pat. Nos. 4,600,006, 4,803,982, 4,884,571 and the like.

These and other objects are achieved by a drill head assembly which is similar to the drill head assembly disclosed in U.S. Patent No. 4,884,571, which is incorporated herein by reference, except that the configuration of the peripheral portions of each of the front cutting edges of the inner drill are modified so as to cause the inner drill to stop its angular rotation more quickly after the inner drill penetrates the bone. In the present invention, the peripheral portions of the front cutting edges of the inner drill are configured so that each front cutting edge includes an axially-projecting portion, the leading edge of which is positioned just radially inward of the outer edge of the front cutting edge, wherein the connecting portion between the leading edge of the axially-projecting portion and the peripheral edge of the front cutting edge recedes rearwardly at a substantially greater angle than the corresponding portion of the drill head assembly taught in U.S. Pat. No. 4,884,571. Preferably, the aforementioned connecting portion takes the form of a tapering radius. By substantially increasing the angle at which the aforementioned connecting portion is disposed, it is possible to minimize any continued angular rotation of the inner drill once it passes through the skull.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts, and further wherein:

FIG. 5 is a schematic enlarged fragmentary elevation view of the cutting end of a drill head assembly formed in accordance with the present invention;

FIG. 6 is a plan view of a bore formed in bone using the drill head assembly of FIG. 5;

FIG. 7 is a schematic enlarged fragmentary elevation view of the cutting end of another drill head assembly formed in accordance with the present invention;

FIG. 8 is a schematic enlarged fragmentary elevation view of the cutting end of yet another drill head assembly formed in accordance with the present invention;

FIG. 9 is a schematic enlarged fragmentary elevation view of the cutting end of still another drill head assembly formed in accordance with the present invention; and FIG. 10 is a schematic enlarged fragmentary elevation view of the cutting end of yet another drill head assembly formed in accordance with the present invention.

DETAILED DESCRIPTION OF THE INVENTION

Figure 1:
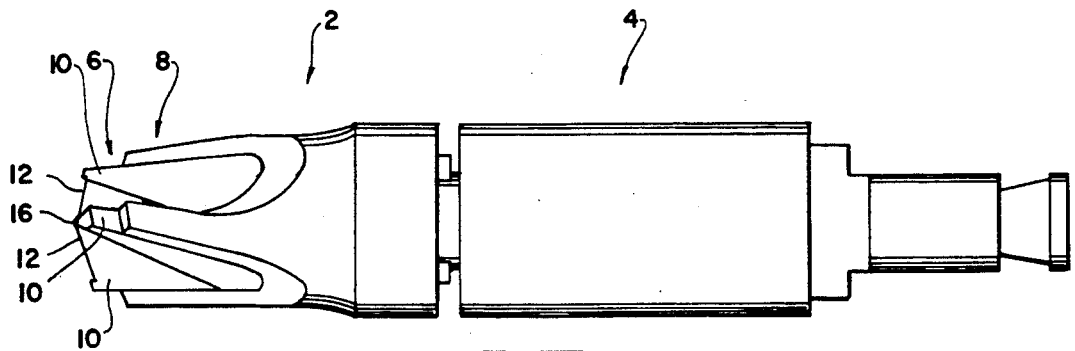
FIG. 1 is a side elevation view of the prior art cranial perforator disclosed in U.S. Pat No. 4,884,571.
Figure 2:
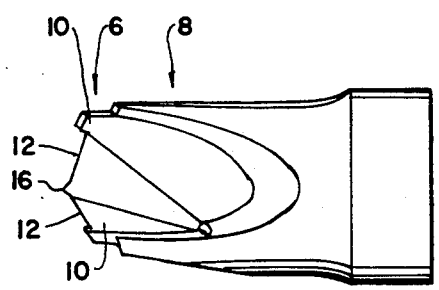
FIG. 2 is a side elevation view of the drill head assembly disclosed in U.S. Pat. No. 4,884,571, the drill head assembly having been rotated 60 degrees from that shown in FIG. 1.
Figure 3:
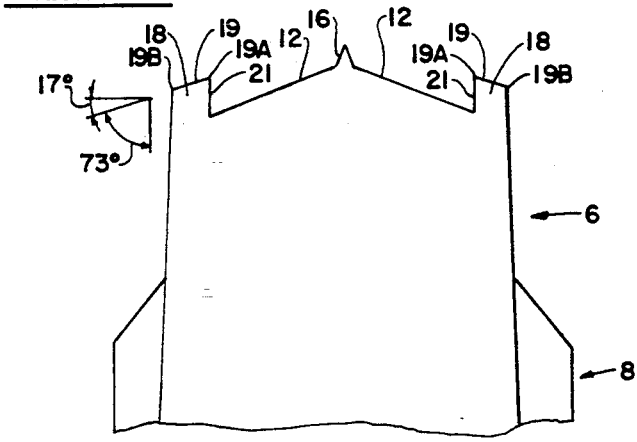
FIG. 3 is a schematic enlarged fragmentary elevation view of the cutting end of the drill head assembly of FIGS. 1 and 2.

Looking first at FIGS. 1-3, there is shown a prior art cranial perforator of the type disclosed in U.S. Pat. No. 4,884,571. The cranial perforator generally comprises a front drill head assembly 2 and a rear support and drive assembly 4. Front drill head assembly 2 generally comprises an inner drill 6 and an outer drill 8. Inner drill 6 comprises a trio of flutes 10, each of which terminates at a front end surface 12. Additionally, the inner drill terminates in a pyramidal front end projection 16 which extends outwardly beyond front end surfaces 12. More specific details on the construction and function of front drill head assembly 2 and rear support and drive assembly 4 are provided in U.S. Pat. No. 4,884,571, which is incorporated herein by reference.

Looking next at FIG. 3, it is important to note that with the prior art front drill head assembly 2 of U.S. Pat. No. 4,884,571, the front end surfaces 12 of inner drill 6 include axially-projecting sections 18 at the peripheral portions of surfaces 12. Surfaces 19 form the front end surfaces of axially-projecting sections 18. Surfaces 19 include an inboard portion 19A and an outboard portion 19B. Surfaces 19 are inclined relative to the longitudinal axis of front drill head assembly 2, so that inboard portions 19A lead outboard portions 19B as the inner drill cuts through the bone. While not specified in U.S. Pat. No. 4,884,571, in practice surfaces 19 have been set at a 17 degree angle relative to the perpendicular radius of the drill head, i.e., at a 73 degree angle relative to the longitudinal axis of the drill head. See FIG. 3. Axially extending surfaces 21 connect inboard portions 19A with the adjoining surfaces 12.

With this construction, when drill head assembly 2 is used to form a bore in a skull, the projecting sections 18 form an annular groove 20 (FIG. 4) at the base of the bore adjacent the sidewall 22 of the bore, with the deepest portion of the annular groove occurring at the radially-innermost edge 24 of the annular groove; pyramidal front point 16 of the inner drill forms a recess 26 at the center of the base of the bore, and drill surfaces 12 of the inner drill form the bone pad 28 in the region between center opening 26 and annular groove 20. With respect to FIG. 4, it is further noted that outer drill 8 will form a counterbore 30 in the bone about the bore formed by inner drill 6.

Figure 4:
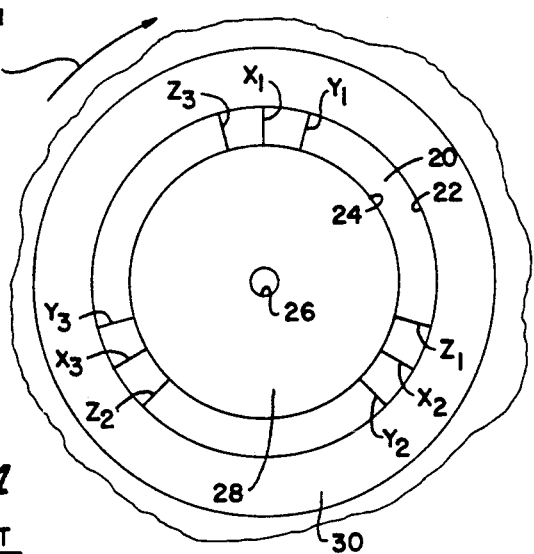
FIG. 4 is a plan view of a bore formed in bone using the drill head assembly of FIGS. 1-3.

Still looking now at FIG. 4, as noted previously, it has been observed that even with the "safety construction" of the cranial perforators of the sort discussed above, the inner drill continues to rotate some angular amount after the inner drill has penetrated the skull. By way of example, suppose that the inner drill forming the bore shown in FIG. 4 breaks through the bone when the leading edges of the flutes are at circumferential location X ($X_1$ being the location of flute 1, $X_2$ being the location of flute 2, and $X_3$ being the location of flute 3). Since the special drive mechanism employed by the perforators requires some additional rotation of the inner drill to cause the engaging portions of the inner drill to withdraw forward out of driving engagement with the rear support and drive assembly, some post-penetration angular rotation of the inner drill (i.e., the "disengagement rotation" discussed above) will take place while the inner drill is positively driven by the rear support and drive assembly 4. This will cause complete openings to be formed in the bone at the base of groove 20, between locations X and Y, with locations Y signifying the positions of the leading edges of the flutes at the moment the inner drill moves out of driving engagement with the rear support and drive assembly. However, as noted previously, since there is also substantial angular momentum resident in the quickly rotating inner drill at the moment the inner drill disengages from the rear support and drive assembly, it has been found that the inner drill will continue to rotate some additional distance (i.e., the "momentum rotation" discussed above) before the inner drill comes to a complete halt. This "momentum rotation" will cause the complete openings formed in the bone at the base of groove 20 to extend further, to some locations Z, with locations Z signifying the positions of the leading edges of the flutes at the moment the inner drill comes to a complete halt. Thus, at the base of groove 20, the axially projecting portions 18 will actually cut through-holes between the locations X and Z for each of the three flutes, the openings between X and Y being attributable to the so-called "disengagement rotation" of the inner drill, and the openings between Y and Z being attributable to the so-called "momentum rotation" of the inner drill. In this regard it will, of course, be appreciated that the precise locations of points Z may vary along the circumference of groove 20 according to the speed of the drill at the moment the inner drill breaches the bone, the specific composition of the bone being drilled, etc. Thus, while the locations of points Z are shown in FIG. 4 to be approximately 60 degrees past the locations of the corresponding points Y (signifying that the so-called "momentum rotation" accounts for about a sixth of a full drill rotation), this should be viewed as exemplary. In practice, it is believed that the so-called "momentum rotation" frequently accounts for a full drill rotation, or even several full rotations, after the inner drill moves out of driving engagement with the rear support and drive assembly and before the drill comes to a complete halt.

The purpose of the present invention is to minimize the size of the openings formed between locations Y and Z, by decreasing the "momentum rotation" of the inner drill.

Looking next at FIG. 5, there is shown an improved drill head assembly 100 formed in accordance with the present invention. Drill head assembly 100 is identical to drill head assembly 2 previously described, except as will be hereinafter described in detail. More specifically, drill head assembly 100 comprises an inner drill 106 and an outer drill 108. Inner drill 106 comprises a trio of flutes 110, each of which terminates at the front end surface 112. Additionally, the inner drill terminates in a pyramidal front end projection 116 which extends outwardly beyond front end surfaces 112. Front end surfaces 112 include axially-projecting sections 118 at the peripheral portions of surfaces 112. Surfaces 119 form the front end surfaces of axially-projecting sections 118. Surfaces 119 include an inboard portion 119A and an outboard portion 119B. Surfaces 119 are inclined relative to the axis of front drill head assembly 100, so that inboard portions 119A lead outboard portions 119B as the inner drill cuts through bone. Axially extending surfaces 121 connect inboard portions 119A with the adjoining surfaces 112.

To the foregoing extent, drill head assembly 100 is identical to drill head assembly 2 previously described. However, drill head assembly 100 differs from drill head assembly 2 with respect to the degree of incline of front surfaces 119 relative to the axis of the front drill head assembly. More specifically, whereas in FIG. 3 surfaces 19 of drill head assembly 2, are shown to be set at a 17 degree angle relative to the perpendicular radius of the drill head (i.e., at a 73 degree angle relative to the longitudinal axis of the drill head), the surfaces 119 of the present invention are set at an angle $\theta$ relative to the perpendicular radius of the drill head, wherein $\theta$ is substantially greater than 17 degrees. Stated another way, the surfaces 119 of the present invention are set at an angle (90-$\theta$) relative to the longitudinal axis of the drill head. While the exact limits of the angle $\theta$ are not currently known, it is believed that in the preferred embodiment surfaces 119 should be set at approximately a 45 degree angle relative to the perpendicular radius of the drill head (i.e., so that the angle $\theta$ is equal to 45 degrees, and so that the angle (90-$\theta$) is equal to 45 degrees). It is also believed that surfaces 119 could be set so that the angle $\theta$ is as little as approximately 25 degrees (and the complementary angle (90-$\theta$) is as great as approximately 65 degrees), or the angle $\theta$ is as great as approximately 65 degrees (and the complementary angle (90-$\theta$) is as little as approximately 25 degrees). The inclination of surfaces 119 are set such that a substantial shoulder of bone will remain adjacent surfaces 119 as the inboard portions 119A of the flutes begin to penetrate completely through the bone. This substantial shoulder of bone is believed to be instrumental in minimizing any continued angular rotation of the inner drill once it passes through the skull. Specifically, while this shoulder of bone is incapable of eliminating the aforementioned "disengagement rotation" of the inner drill (i.e., that portion of the post-penetration angular rotation of the inner drill associated with the disengagement of the inner drill from the rear support and drive assembly), it has been found to be capable of eliminating substantially all of the "momentum rotation" of the inner drill (i.e., that portion of the post-penetration angular rotation of the inner drill associated solely with the angular momentum stored in the inner drill at the moment the inner drill becomes fully disengaged from the rear support and drive assembly).

With this construction, when drill head assembly 100 is used to form a bore in a skull, the projecting sections 118 form an annular groove 120 (FIG. 6) at the base of the bore adjacent to sidewall 122 of the bore, with the deepest portion of the annular groove occurring at the radially-innermost edge 124 of the annular groove; pyramidal front point 116 of the inner drill forms a recess 126 at the center of the base of the bore, and drill surfaces 112 of the inner drill cut the bone pad 128 in the region between center opening 126 and annular groove 120. With respect to FIG. 6, it is further noted that outer drill 108 will form a counterbore 130 in the bone about the bore formed by inner drill 106.

Still looking now at FIG. 6, suppose that the inner drill forming the bore shown in FIG. 6 breaks through the bone when the leading edges of the flutes are at circumferential location X. Since the special drive mechanism employed by the perforator requires some additional rotation of the inner drill to cause the engaging portions of the inner drill to withdraw forward out of driving engagement with the rear support and drive assembly, some post-penetration angular rotation of the inner drill (i.e., the "disengagement rotation" discussed above) will take place while the inner drill is positively driven by the rear support and drive assembly. This will cause complete openings to be formed in the bone at the base of groove 120, between locations X and Y, with locations Y signifying the positions of the leading edges of the flutes at the moment the inner drill moves out of driving engagement with the rear support and drive assembly.

At this point, however, the substantial shoulder of bone formed adjacent surfaces 119 will act as a brake on the still-rotating inner drill to rapidly bring the inner drill to a complete stop. Thus, the complete openings formed in the bone will extend only slightly beyond locations Y, to some locations Z, with locations Z signifying the positions of the leading edges of the flutes at the moment the inner drill comes to a complete halt. Accordingly, while at the base of groove 120 the axially projecting portions 118 will cut all the way through the bone between the locations X and Z for each of the three flutes (the openings between X and Y being attributable to the so-called "disengagement rotation" of the inner drill, and the openings between Y and Z being attributable to the so-called "momentum rotation" of the inner drill), the difference between the size of the openings between X and Z will actually be only slightly greater than the size of the openings between X and Y. In this regard, it should be noted that while in FIG. 6 the locations of points Z are shown to be approximately 5 degrees past the locations of the corresponding points Y, this should be viewed as exemplary of the effect being observed, since in practice it can be something more or less than that shown in the drawing.

Thus, it will be seen that by varying the inclination of surfaces 119 with respect to the axis of the drill head assembly, the post-penetration rotation of the drill attributable to "momentum rotation" can be substantially eliminated.

FIG. 7 shows another front drill head assembly 200. Drill head assembly 200 is identical to drill head assembly 100 previously described, except that surfaces 221, which connect inboard portions 219A with the adjoining surfaces 212, are not disposed parallel to the longitudinal axis of the drill head assembly. Preferably, surfaces 221 are disposed so as to mirror surfaces 219 about an axially-extending line passing through portions 219A, in the manner shown in FIG. 7.

Drill head assembly 200 is believed to provide all of the advantages of drill head assembly 100, i.e., substantially instantaneous stopping of the inner drill once the safety mechanism halts driving rotation of the inner drill.

Looking next at FIG. 8, there is shown a preferred form of drill head assembly 300 formed in accordance with the present invention. Drill head assembly 300 is identical to the drill head assembly 100, except as will be hereinafter described and illustrated. More specifically, drill head assembly 300 comprises an inner drill 306 and an outer drill 308. Inner drill 306 comprises a trio of flutes 310, each of which terminates in a front end surface 312. Additionally, front end surfaces 312 each include a notch 313, and the inner drill terminates in a pyramidal front end projection 316 which extends outwardly beyond front end surfaces 312. Front end surfaces 212 include axially-projecting sections 318 at the peripheral portions of surfaces 312. Surfaces 319 and 321 form the front end surfaces of axially projecting sections 318. Surfaces 319 are curved along their length and include an inboard portion 319A and an outboard portion 319B. Inboard portions 319A adjoin surfaces 321, which are also curved along their length. Inner drill member 306 is formed so that the extent of curvature of surfaces 319 results in an average angle $\theta$ (i.e., as measured along an axis extending between the end of inboard portion 319A to the end of outboard portion 319B) of substantially greater than 17 degrees. Preferably surfaces 319 are formed so that the angle $\theta$ is equal to 45 degrees, although it is believed that drill head assembly 300 will function satisfactorily when $\theta$ is as little as approximately 25 degrees or as great as approximately 65 degrees. Surfaces 321 are formed so that the extent of curvature of these surfaces also results in an average angle $\theta$ (i.e., as measured along an axis extending between where surfaces 321 meet surfaces 319 to where surfaces 321 connect with adjoining surfaces 312).

Drill head assembly 300 provides all of the advantages of drill head assembly 100, i.e., substantially instantaneous stopping of the inner drill once the safety mechanism halts driving rotation of the inner drill. In addition, drill head assembly 300 provides the additional advantage that its axially-projecting sections 318 cut in a rounded manner so as to avoid sharp edges.

Looking next at FIG. 9, there is shown yet another form of drill head assembly 400 formed in accordance with the present invention. Drill head assembly 400 is identical to drill head assembly 300, except that surface 421 is formed with a flat profile. Preferably, surface 421 is set at the aforementioned angle $\theta$.

Cranial perforator 400 provides all of the advantages of perforator 100, i.e., substantially instantaneous stopping of the inner drill once the safety mechanism halts driving rotation of the inner drill. In addition, cranial perforator 400 provides the additional advantage that its outboard portion 419 cuts in a rounded manner so as to avoid sharp edges.

FIG. 10 shows yet another front drill head assembly 500. Drill head assembly 500 is identical to front drill head assembly 400, except that surface 521 is set substantially parallel to the axis of the drill head.

Cranial perforator 500 provides all of the advantages of perforator 100, i.e., substantially instantaneous stopping of the inner drill once the safety mechanism halts driving rotation of the inner drill. In addition, cranial perforator 500 provides the additional advantage that its outboard portion 519 cuts in a rounded manner so as to avoid sharp edges.

Since certain changes may be made in the above embodiments without departing from the scope of the invention herein involved, it is intended that all matter contained in the above description or shown in the accompanying drawings shall be interpreted in an illustrative and not in a limiting sense.

Thus, for example, it is anticipated that drill head assemblies 100, 200, 300, 400 and 500 might be formed with more or less than the three flutes disclosed, e.g. they might be formed with only one flute, or they might be formed with four flutes.

Numerous advantages are obtained by utilizing the present invention.

For one thing, a new and improved drill head assembly for "safety construction" cranial perforators is provided which will minimize any continued angular rotation of the inner drill after it passes through the skull.

For another thing, a new and an improved drill head assembly for "safety construction" cranial perforators is provided which will substantially eliminate the aforementioned post-penetration "momentum rotation" of the inner drill.

In addition, a new and improved drill head for "safety construction" cranial perforators is provided which will yield a thicker and stronger shoulder of bone adjacent the peripheral portion of the front cutting edge of the inner drill to impede further progress of the inner drill toward the brain once the drill members are disengaged from the drive assembly.

In addition, a new and improved drill head assembly is provided which may be used with cranial perforators of the type disclosed in U.S. Pat. Nos. 4,600,006, 4,803,982, 4,884,571 and the like.

What is claimed is:

1. A cranial perforator comprising:
   (1) a drill head assembly comprising (a) an inner drill having a plurality of inner cutting flutes, each terminating in a first cutting edge, and (b) an outer drill comprising a plurality of outer cutting flutes, each terminating in a second cutting edge, wherein each of said first cutting edges includes an axially-projecting section adjacent the radially-outermost portion of said first cutting edge which projects forwardly of adjacent portions of said first cutting edge, the forward-most portion of said projecting section being positioned radially inwardly of the radially-outermost portion of said first cutting edge; and
   (2) drive means for enabling said drill head assembly when said inner drill is encountering a resistive surface, and disabling said drill head assembly when said inner drill is no longer encountering said resistive surface while said outer drill is still encountering said resistive surface.

2. A cranial perforator according to claim 1 wherein each of said projecting sections has a curved configuration.

3. A cranial perforator according to claim 1 wherein said inner drill comprises a pyramidal projection positioned on the axis of rotation of said inner drill, and further wherein the forward-most portion of said pyramidal projection extends forwardly of said forward-most portions of said projecting section.

4. A cranial perforator according to claim 1 wherein each of said projecting sections has a straight configuration.

5. A cranial perforator according to claim 1 wherein each of said first cutting edges has a straight configuration.

6. A cranial perforator comprising:
   (1) a drill head assembly for forming a bore in a skull, said drill head assembly comprising (a) an inner drill having a plurality of inner cutting flutes, each terminating in a first end surface, and (b) an outer drill comprising a plurality of outer cutting flutes, each terminating in a second end surface, wherein each of said inner cutting flutes includes a segment which projects forwardly of the radially-outermost portion of said first end surface, said segments being designed to form a peripheral annular groove in said skull at the base of said bore, the deepest portion of said annular groove being positioned radially-inwardly of the sidewall of that portion of said bore formed by said inner drill; and
   (2) drive means for enabling said drill head assembly when said inner drill is encountering a resistive surface, and disabling said drill head assembly when said inner drill is no longer encountering said resistive surface while said outer drill is still encountering said resistive surface.

7. A perforator according to claim 6 wherein each of said segments include a front end surface which is contiguous with said first end surface.

8. A perforator according to claim 7 wherein each of said front end surfaces of said segments has a curved configuration.

9. A cranial perforator comprising:
   (1) a drill head assembly comprising (a) an inner drill having a plurality of inner cutting flutes, each comprising first and second cutting edges, and (b) an outer drill comprising a plurality of outer cutting flutes, each terminating in a third cutting edge, wherein each of said second cutting edges intersects the radially-outermost portion of a corresponding respective one of said inner cutting flutes, and further wherein each of said second cutting edges extends along an axis which is inclined at an angle Q with respect to the rotational axis of said inner drill, wherein Q is less than about 65°; and
   (2) drive means for enabling said drill head assembly when said inner drill is encountering a resistive surface, and disabling said drill head assembly when said inner drill is no longer encountering said resistive surface while said outer drill is still encountering said resistive surface.

10. A cranial perforator according to claim 9 wherein the forward-most portion of each of said second cutting edges is positioned radially inward of said radially-outermost portion of a corresponding respective one of said inner cutting flutes.

11. A cranial perforator according to claim 9 wherein said angle Q ranges from about 25° to about 65°.

12. A cranial perforator according to claim 9 wherein each of said inner cutting flutes comprises a fourth non-cutting edge extending between said first and second cutting edges.

13. A perforator according to claim 9 wherein each of said inner cutting flutes comprises a fifth cutting edge extending between said first and second cutting edges.

14. A cranial perforator comprising:
   (1) a drill head assembly comprising (a) an inner drill having a plurality of inner cutting flutes, each comprising first and second cutting edges, and (b) an outer drill comprising a plurality of outer cutting flutes, each terminating in a third cutting edge, wherein each of said second cutting edges intersects the radially-outermost portion of a corresponding respective one of said inner cutting flutes, and further wherein each of said second cutting edges extends along an arc having an average slope which is inclined at an angel Q with respect to the rotational axis of said inner drill, said average slope being measured along an axis intersecting the forward-most and rearward-most portion of said second cutting edges, and further wherein Q is less than about 65°, and further wherein the innermost end of said second cutting edge is located forwardly of the outermost end of said first cutting edge; and (2) drive means for enabling said drill head assembly when said inner drill is encountering a resistive surface, and disabling said drill head assembly when said inner drill is no longer encountering said resistive surface while said outer drill is still encountering said resistive surface.

15. A cranial perforator according to claim 14 wherein the forward-most portion of each of said second cutting edges is positioned radially inward of said radially-outermost portion of a corresponding respective on of said inner cutting flutes.

16. A cranial perforator according to claim 14 wherein said angle Q ranges from about 25° to about 65°.

17. A drill head assembly comprising inner and outer drills for use with a cranial perforator comprising drive means for enabling said drill head assembly when said inner drill is encountering a resistive surface and disabling said drill head assembly when said inner drill is no longer encountering said resistive surface while said outer drill is still encountering said resistive surface, and further wherein:
(a) said inner drill includes a plurality of inner cutting flutes, each comprising first and second cutting edges, wherein each of said second cutting edges intersects the radially-outermost portion of a corresponding respective one of said inner cutting flutes, and further wherein each of said second cutting edges extends along an axis which is inclined at an angle Q with respect to the rotational axis of said inner drill, wherein Q is less than about 65°; and
(b) said outer drill comprises a plurality of outer cutting flutes, each terminating in a third cutting edge.

18. A cranial perforator comprising:
(1) a drill head assembly comprising (a) an inner drill having a plurality of inner cutting flutes, each comprising a first cutting edge, and (b) an outer drill comprising a plurality of outer cutting flutes, each terminating in a second cutting edge, wherein each of said inner cutting flutes comprises an axially-projecting portion intersecting the radially-outermost portion of said inner cutting flute, and wherein each of said axially-projecting portions comprises a third cutting edge which extends from the radially-outermost portion of said inner cutting flute along an axis which is inclined at an angle Q with respect to the rotational axis of said inner drill, wherein Q is less than about 65°, and further wherein the radially-innermost end of said third cutting edge is located forwardly of the radially-outermost end of said third cutting edge and forwardly of the radially-outermost end of said first cutting edge; and (2) drive means for enabling said drill head assembly when said inner drill is encountering a resistive surface, and disabling said drill head assembly when said inner drill is no longer encountering said resistive surface while said outer drill is still encountering said resistive surface.

19. A cranial perforator comprising:
(1) a drill head assembly comprising (a) an inner drill having a plurality of inner cutting flutes, each comprising first and second cutting edges, and (b) an outer drill comprising a plurality of outer cutting flutes, each terminating in a third cutting edge, wherein each of said second cutting edges intersects the radially-outermost portion of a corresponding respective one of said inner cutting flutes, and further wherein each of said second cutting edges extends along an arc having an average slope which is inclined at an angle Q with respect to the rotational axis of said inner drill, said average slope being measured along an axis intersecting the forward-most and rearward-most portions of said second cutting edges, and further wherein Q is less than about 65°, and further wherein each of said inner cutting flutes comprises a fourth non-cutting edge extending between said first and second cutting edges; and (2) drive means for enabling said drill head assembly when said inner drill is encountering a resistive surface, and disabling said drill head assembly when said inner drill is no longer encountering said resistive surface while said outer drill is still encountering said resistive surface.

20. A cranial perforator comprising:
(1) a drill head assembly comprising (a) an inner drill having a plurality of inner cutting flutes, each comprising first and second cutting edges, and (b) an outer drill comprising a plurality of outer cutting flutes, each terminating in a third cutting edge, wherein each of said second cutting edges intersects the radially-outermost portion of a corresponding respective one of said inner cutting flutes, and further wherein each of said second cutting edges extends along an arc having an average slope which is inclined at an angel Q with respect to the rotational axis of said inner drill, said average slope being measured along an axis intersecting the forward-most and rearward-most portions of said second cutting edges, and further wherein Q is less than about 65°, and further wherein each of said inner cutting flutes comprises a fourth cutting edge extending between said first and second cutting edges; and (2) drive means for enabling said drill head assembly when said inner drill is encountering a resistive surface, and disabling said drill head assembly when said inner drill is no longer encountering said resistive surface while said outer drill is still encountering said resistive surface.

* * * * *

UNITED STATES PATENT AND TRADEMARK OFFICE
CERTIFICATE OF CORRECTION

PATENT NO. : 5,135,532

DATED : August 4, 1992

INVENTOR(S) : John W. Baker

It is certified that error appears in the above-identified patent and that said Letters Patent is hereby corrected as shown below:

Claim 14, column 11, line 4, the word "portion" should be -- portions --;

Claim 15, column 11, line 20, the word "on" should be -- one --; and

Claim 20, column 12, line 46, the word "angel" should be -- angle --.

Signed and Sealed this

Tenth Day of August, 1993

Attest:

MICHAEL K. KIRK

*Attesting Officer*      Acting Commissioner of Patents and Trademarks